United States Patent [19]

Marumoto et al.

[11] 4,255,565
[45] Mar. 10, 1981

[54] PRODUCTION OF 2,6-DIAMINONEBULARINES

[75] Inventors: Ryuji Marumoto; Shunsuke Shima, both of Minoo; Yoshiyasu Furukawa, Toyonaka, all of Japan

[73] Assignee: Takeda Chemical Industries, Ltd., Osaka, Japan

[21] Appl. No.: 953,255

[22] Filed: Oct. 20, 1978

[30] Foreign Application Priority Data

Oct. 21, 1977 [JP] Japan .................... 52-127147

[51] Int. Cl.³ .................................. C07H 17/00
[52] U.S. Cl. .................................. 536/24; 424/180; 536/23
[58] Field of Search .................. 536/24, 23

[56] References Cited
U.S. PATENT DOCUMENTS

| 3,544,554 | 1/1970 | Koch et al. ............... 536/26 |
| 3,936,439 | 2/1976 | Maromuto et al. ........ 536/24 |

FOREIGN PATENT DOCUMENTS 42-10518 7/1967 Japan .
1390014 4/1975 United Kingdom .

Primary Examiner—Johnnie R. Brown
Assistant Examiner—Blondel Hazel
Attorney, Agent, or Firm—Wenderoth, Lind & Ponack

[57] ABSTRACT

Compounds of the formula

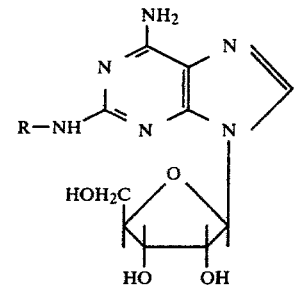

wherein R is a phenyl or cyclohexyl group which may be substituted by halogen, lower alkyl or lower alkoxy, or their acid addition salts, are produced in good yield by reacting a compound of the formula

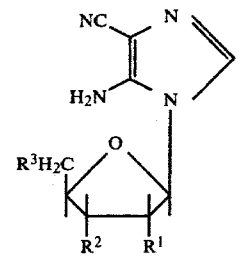

wherein $R^1$, $R^2$ and $R^3$, independently of each other, are a hydroxyl group which may be proctected, which is prepared in 2 or 3 steps from 5-amino-1-β-D-ribofuranosylimidazole-4-carboxamide, with a compound of the formula

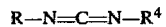

R—N=C=N—R⁴ wherein R has the same meaning as defined above and $R^4$ is hydrogen or the same group as R, and, if necessary, subjecting the resulting compound to a treatment for removal of protective groups on its hydroxyl groups.

10 Claims, No Drawings

PRODUCTION OF 2,6-DIAMINONEBULARINES

The present invention relates to a novel and improved method for producing 2,6-diaminonebularines. More particularly, the present invention relates to a commercially profitable method for producing N²-substituted-2,6-diaminonebularines of the formula

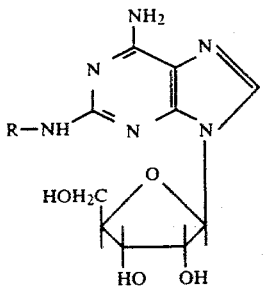
(I)

wherein R is a phenyl or cyclohexyl group which may be substituted by halogen, lower alkyl or lower alkoxy and salts thereof.

The above-mentioned compounds (I) and their salts have excellent coronary vasodilator and platelet aggregation inhibitor actions and, as such, are of value as coronary vasodilators, platelet aggregation inhibitors, and the like. (Refer to U.S. Pat. No. 3,936,439 issued on Feb. 3, 1976). The hitherto-known processes for the production of the above-mentioned compounds (I) are the process comprising reacting a 2-halogenoadenosine with an amine of the formula R—NH₂ wherein R has the same meaning as defined hereinbefore, and the process comprising the steps of reacting a 2-halogenoinosine with the above-mentioned amine, to prepare a 2-substituted amino-inosine, replacing the 6-hydroxyl group thereof with a reactive group (e.g. halogen, mercapto or alkylmercapto) and subjecting the same to ammonolysis (Refer to the U.S. patent mentioned above.). However, these known processes invariably require at least six reaction steps from the starting material 5-amino-1-β-D-ribofuranoxylimidazole-4-carboxamide (hereinafter referred to briefly as AICAr), which is a fermentation product, to the final compound (I) and give the compound (I) only in unsatisfactory yields. Moreover, these processes have the disadvantage of involving the use of intermediates which are not easy to handle.

Under the above-mentioned technical situation, the present inventors carried out extensive research to develop a more industrially profitable method for producing the compound (I), and have unexpectedly found that the compound (I) can be produced in good yield by reacting a compound of the formula

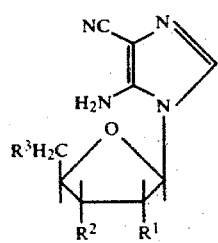
(II)

wherein R¹, R² and R³, independently of each other, are a hydroxyl group which may be protected, which is easy to handle and can be prepared in good yield via 2 or 3 steps from AICAr, with a compound of the formula $$R-N=C=N-R^4$$ (III)

wherein R has the same meaning as defined above and R⁴ is hydrogen or the same group as R, and if necessary, subjecting the resulting compound to a treatment for removal of protective groups on its hydroxyl groups. This finding was followed by further research which has culminated in the establishment of the present invention.

Thus, in accordance with the first aspect of the present invention, this invention provides a method for producing the compound (I) in good yield, which comprises reacting a compound (II) with a compound (III) and, if necessary, subjecting the resulting compound to a treatment for removal of the protective groups.

In accordance with the second aspect, the present invention provides a method for producing the compound (I) in good yield in 3 or 4 steps by way of the compound (II) from AICAr. Other objects of the present invention will be made clear from the description and claims presented hereinafter.

Referring to the formula (II), protective groups on protected hydroxyls for R¹, R² and R³ may for example be carboxylic acid-derived acyl groups which may be aliphatic, aromatic, heterocyclic, saturated or unsaturated and which may be exemplified by acetyl, propionyl, caproyl, palmitoyl, benzoyl, toluoyl, furoyl, etc.; nitro; sulfonyl; isopropylidene; alkoxyalkylidene; and the like. Among these protective groups, acyl groups derived from aliphatic or aromatic carboxylic acids containing up to 7 carbon atoms are preferred and propionyl is the most desirable in view of the advantages mentioned hereinafter. All of R¹, R² and R³ may be protected, or some of them, e.g. R² and R³, are protected, or all of R¹, R² and R³ may be unprotected hydroxyls; in the last case the compound (II) being 5-amino-1-β-D-ribofuranosyl-4-cyanoimidazole.

Referring to the formula (III), R is a phenyl or cyclohexyl group which may be substituted by halogen, lower alkyl or lower alkoxy. The halogen may for example be chlorine, bromine or iodine. The lower alkyl may be a straight-chain or branched alkyl group such as methyl, ethyl, propyl, isopropyl, n-butyl, t-butyl or hexyl. Particularly desirable is an alkyl group containing up to 4 carbon atoms. The lower alkoxy may be a straight-chain or branched alkoxy group such as methoxy, ethoxy, propoxy, isopropoxy, n-butoxy, t-butoxy, hexoxy or the like. Particularly desirable are alkoxy groups of up to 4 carbon atoms. The phenyl and cyclohexyl groups may have one or more of the above-mentioned substituents in optional positions on the respective rings.

R⁴ in the formula (III) is either hydrogen or the same group as R. Thus, this formula (III) encompasses both cyanamides which may be shown also by the tautomeric formula RNHCN wherein R has the same meaning as defined above, and carbodiimides. Such cyanamides can be easily obtained, for example by the procedure described in Berichte der Deutschen Chemischen Gesellschaft 18, 3217–3234(1885) or a procedure analogous thereto, while the carbodiimides can also be easily obtained, for example by the procedure described in Journal of Organic Chemistry 32, 2895 (1967) or a procedure analogous thereto.

The compound of the formula (III) wherein R is unsubstituted phenyl and R⁴ is hydrogen, that is phenylcyanamide, may be employed in the form of its trimer, such as triphenylmelamine:

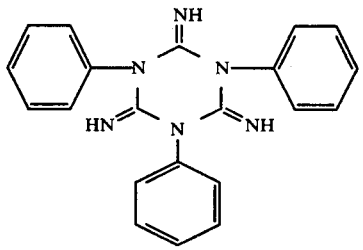

[Refer to Annalen der Chemie 384, 350-351(1911)] or Hofmann's triphenylisomelamine which is a molecular compound consisting of 2 moles of said triphenylmelamine and 1 mole of phenylcyanamide [Refer to the literature mentioned just above and the above-mentioned Berichte der Deutschen Chemischen Gesellschaft 18, 3217-3234(1885)].

In reacting a compound (II) with a compound (III) according to this invention, it is generally advantageous to employ at least one molar equivalent, preferably about 2 to 5 molar equivalents, of compound (III) with respect to compound (II). Generally, this reaction is desirably conducted in the presence of a base. As examples of the base there may be mentioned ammonia and primary to tertiary amines (including cyclic amines; and, preferably, having low boiling points; e.g. n-propylamine, isopropylamine, n-butylamine, triethylamine, pyridine, picoline, 2,6-lutidine, etc.), sodium and potassium alkoxides (e.g. sodium methoxide, sodium ethoxide, sodium methoxyethoxide, potassium tert.-butoxide, etc.), with ammonia being the most advantageous. Normally such a base is preferably employed in a proportion of about 10 to 100 molar equivalents relative to compound (II). Generally this reaction is preferably conducted in a solvent. The solvent may be any organic solvent that does not interfere with the contemplated reaction. Thus, for example, lower alkanols (e.g. methanol, ethanol, propanol, etc.), tetrahydrofuran, dioxane or dimethylformamide, as well as mixtures thereof, may be employed with advantage. Generally this reaction proceeds satisfactorily at elevated temperatures, i.e. about 100° to 200° C., and is advantageously carried out in a gas-tight reactor.

The protective groups on protected hydroxyls of the compound (II) normally detach themselves as the compound (II) undergoes reaction with the compound (III) but, if the resulting compound still bears the protective groups, such groups can be easily removed by techniques known per se, whereupon the object compound (I) is obtained. Such techniques may be exemplified by treatment with a base (e.g. aqueous ammonia or alkali metal alkoxide) in the case of carboxylic acid-derived acyl groups, catalytic reduction in the case of nitro, or treatment with an acid (e.g. formic acid, acetic acid or hydrochloric acid) in the case of isopropylidene groups.

As mentioned above, the present invention further encompasses a method for producing the compound (I) in good yield from AICAr in 3 or 4 steps by way of a compound (II) which is easy to handle. Thus, the invention provides a method for producing a compound (I), which comprises subjecting AICAr to a reaction for protecting its hydroxyl groups, subjecting the resulting hydroxyl-protected AICAr to dehydration reaction to yield a compound of the formula

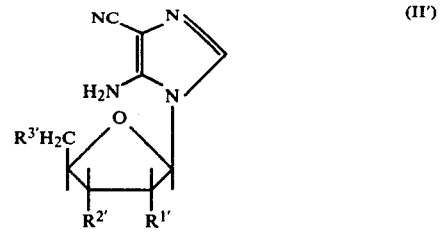

wherein $R^{1'}$, $R^{2'}$ and $R^{3'}$, independently of each other, are a protected hydroxyl group, reacting the resulting compound (II') with a compound (III), either after or without a prior treatment for removal of the protective groups, and, if necessary, subjecting the resulting compound to a treatment for removal of the protective groups.

In this process, the step of subjecting AICAr to reaction for protecting its hydroxyl groups can be conducted by reacting AICAr with a reactive derivative of a carboxylic acid or sulfonic acid, nitric acid, a ketone, an aldehyde, an ortho-ester or the like which corresponds to the protective groups on protected hydroxyls, $R^{1'}$, $R^{2'}$ and $R^{3'}$. These protective groups are the same groups as the protective groups mentioned hereinbefore in connection with $R^1$, $R^2$ and $R^3$. The carboxylic acids employable in this step may be aliphatic, aromatic, heterocyclic, saturated or unsaturated, thus, include acetic acid, propionic acid, acrylic acid, butyric acid, caproic acid, palmitic acid, benzoic acid, toluic acid, furonic acid, and the like. Among these carboxylic acids, aliphatic or aromatic carboxylic acids containing up to 7 carbon atoms are preferred. Such a carboxylic acid is normally employed in the form of a reactive derivative with respect to its carboxyl function, such as the halide, e.g. chloride or bromide, or acid anhydride. With respect to AICAr, such a reactive derivative of carboxylic acid is desirably employed in a proportion of at least about 3 molar equivalents and, preferably, about 5 to 15 molar equivalents. Generally the reaction between AICAr and said reactive carboxylic acid derivative is preferably conducted in a solvent. This solvent may be of any type only if it does not interfere with the contemplated reaction. For example, benzene, halogenated hydrocarbon solvents such as chloroform, organic bases such as pyridine, and acidic solvents such as the aforementioned carboxylic acids themselves may be employed with advantage. While the reaction generally proceeds fast enough at room temperature, it may be conducted at elevated or reduced temperatures in order to control the reaction velocity.

The reaction of AICAr with nitric acid, e.g. fuming nitric acid, is conducted at a temperature between −30° C. and +20° C., preferably within the range of 0° C. to 20° C. It is desirable to employ a large excess of fuming nitric acid.

The reaction of AICAr with a reactive sulfonic acid derivative, such as a sulfonyl chloride (e.g. methanesulfonyl chloride or toluenesulfonyl chloride), is preferably conducted in an organic solvent, e.g. pyridine, normally using 3 to 10 molar equivalents of sulfonyl chloride with respect to AICAr. Desirably this reaction is carried out at temperatures in the range of 10° C. to 30° C.

The reaction of AICAr with said aldehyde, ketone or ortho-ester is conducted by permitting a large excess, preferably about 10 to 100 molar equivalents, of said aldehyde, ketone or otho-ester to act on AICAr, preferably in the presence of an acid catalyst such as a mineral acid (e.g. sulfuric acid, hydrochloric acid or phosphoric acid), a Lewis acid (e.g. zinc chloride or aluminum chloride) or toluenesulfonic acid. If necessary, this reaction may be conducted in an organic solvent that does not interfere with the reaction, N,N-dimethylformamide, dimethylacetamide, dioxane and ethers being examples of the solvent. Desirably the reaction is carried out at a temperature within the range of about 0° C. to 30° C.

Among the hydroxyl-protected AICAr thus obtainable, 5-amino-1-[2,3,5-tri-O-(carboxylic acid-derived acyl)-β-D-ribofuranosyl]imidazole-4-carboxamides are preferred. Especially, 5-amino-1-(2,3,5-tri-O-propionyl-β-D-ribofuranosyl)-imidazole-4-carboxamide, which is a novel compound, can be easily obtained as crystals having a relatively high melting point, thus being particularly valuable for the purposes of the present invention.

According to the process of the present invention, the above hydroxyl-protected AICAr is subjected to dehydration reaction to yield the compound (II'). This dehydration reaction may be conducted by any optional procedure only if the 4-carboxamide group of the hydroxyl-protected AICAr can thereby be transformed into a carbonitrile group. Thus, for example, it is advantageous to permit a dehydrating agent to act on the hydroxyl protected AICAr in the presence of an organic base. As examples of said dehydrating agent there may be mentioned halogenated phosphorus compounds (e.g. phosphorus oxychloride, phosphorus trichloride, phosphorus pentachloride, etc.) and acid chlorides (e.g. acetyl chloride, benzoyl chloride, thionyl chloride, p-toluenesulfonyl chloride, methanesulfonyl chloride, carbobenzoxy chloride, etc.). Such a dehydrating agent is desirably employed in a proportion of at least one molar equivalent, preferably about 1.2 to 2 molar equivalents, with respect to the hydroxyl-protected AICAr. As examples of said organic base there may be mentioned trimethylamine, triethylamine, tri-n-butylamine, picoline, collidine, 2,6-lutidine and pyridine. Such an organic base is desirably employed in a proportion of at least one molar equivalent, preferably about 5 to 10 molar equivalents, with respect to the hydroxyl-protected AICAr. Generally this reaction is desirably conducted in the presence of a solvent. Preferred examples of such solvent are chloroform, dichloromethane, tetrahydrofuran and dioxane. While the reaction proceeds fast enough at room temperature, the reaction may be conducted at an elevated or reduced temperature within the range of about 0° C. to 50° C. for the purpose of controlling the reaction velocity.

The resulting compound (II'), either after being subjected to the de-protecting treatment mentioned hereinbefore in connection with the protected hydroxyls R¹, R² and R³ or without such a prior treatment, is subjected to the reaction with compound (III) mentioned above. In this connection, it is to be noted that the formula (II) mentioned hereinbefore includes both the compound (II') per se and the de-protected product from the compound (II'). In the case where the resultant product of the reaction between the compound (II) and the compound (III) still bears protective groups, it is further subjected to the above-mentioned de-protecting treatment, whereupon the object compound (I) is obtained. From a practical point of view, it is advantageous to subject the compound (II') to the de-protecting treatment to yield 5-amino-1-β-D-ribofuransoyl-4-cyanoimidazole, and then reacting the resultant 5-amino-1-β-D-ribofuranosyl-4-cyanoimidazole with the compound (III).

N²-Substituted-2,6-diaminonebularine (I) thus produced can be easily separated from the reaction mixture by procedures known per se. For example, after the excess reactant and solvent are distilled off, the residue is washed with a lower alkanol or the like and recrystallized from water, a lower alkanol or a mixture thereof, whereby the compound (I) can be obtained in pure form. This compound (I) can also be isolated as a physiologically acceptable acid addition salt i.e. inorganic acid salt (e.g. hydrochloride or sulfate) or organic acid salt (e.g. acetate, citrate or tartrate) by procedures known per se.

The following Reference Example and Examples are intended merely to illustrate presently preferred embodiments of the present invention and not to restrict the scope of this invention.

Throughout the foregoing description as well as in the following Reference Example, Examples and Claims, "g.", "kg.", "ml.", "l.", "°C.", "N" and "M" respectively refer to "gram(s)", "kilogram(s)", "milliliter(s)", "liter(s)", "degrees centigrade" "Normal(s)" and "Molar concentration".

REFERENCE EXAMPLE

In 100 ml. of water was dissolved 20.8 g. of p-bromoaniline hydrochloride and, following addition of 11 g. of potassium thiocyanate, the solution was heated on a boiling water bath for 2 hours.

The crystals separating out when cold were recovered by filtration, washed and dried to obtain 9 g. of p-bromophenylthiourea. This product was dissolved in 150 ml. of 10% aqueous potassium hydroxide and, following addition of 30 g. of lead acetate, the solution was stirred at room temperature for 15 minutes and, then, heated on a water bath at 80° C. for 15 minutes. the precipitated lead sulfide was filtered off and the filtrate was neutralized with acetic acid when hot. Upon cooling, 5 g. of p-bromophenylcyanamide separated out as crystals melting at 112°–113° C.

The N-substituted cyanamides described below in Table 1 were synthesized in the same manner as above.

TABLE 1

| R—NHCN | |
|---|---|
| R | Melting point (°C.), Infrared absorption spectrum |
|  | 38 |
| 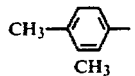 | 69 |
| 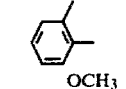 | 75–76 |
| 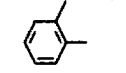 | 77–78 |

TABLE 1-continued

| R | R—NHCN Melting point (°C.), Infrared absorption spectrum |
|---|---|
| 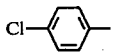 4-Cl-C₆H₄ | 105–106 |
| 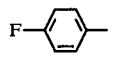 4-F-C₆H₄ | 83–84 |
| 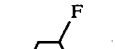 2-F-C₆H₄ | 84–85 |
| 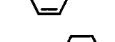 4-C₂H₅-C₆H₄ | Oil, 2220cm⁻¹(—CN) |
| 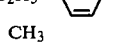 2-CH₃-C₆H₄ | Oil, 2230cm⁻¹(—CN) |
|  2-CH₃O-C₆H₄ | Oil, 2220cm⁻¹(—CN) |
| 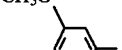 2-F-C₆H₄ | 57 |
|  2-Cl-C₆H₄ | 82–84 |
| 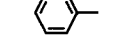 2-Br-C₆H₄ | 86–87 |
| 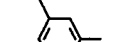 3-CH₃-C₆H₄ | 75–76 |
| 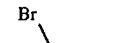 3-Cl-4-CH₃-C₆H₃ | 105–106 |
| 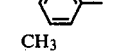 3,4-(CH₃O)₂-C₆H₃ | 107–109 |
| 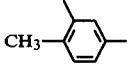 3-Cl-4-CH₃O-C₆H₃ | 66–68 |
| 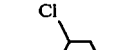 4-n-C₄H₉-C₆H₄ | Oil, 2230cm⁻¹(—CN) |
| 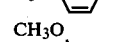 3,5-(CH₃)₂-C₆H₃ | 105–106 |
| 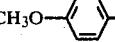 3,5-(CH₃)₂-C₆H₃ | 121–122 |
| 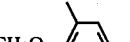 3,4-(CH₃)₂-C₆H₃ | 106–108 |
| 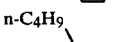 4-Cl-2-OCH₃-C₆H₃ | 142–143 |
| 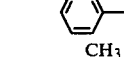 2,3-Cl₂-C₆H₃ | 150–151 |
| 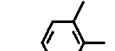 2,5-Cl₂-C₆H₃ | 139 |

EXAMPLE 1

(1) In a mixture of 350 ml. of pyridine and 400 ml. of propionic anhydride, 258 g. of 5-amino-1-β-D-ribofuranosylimidazole-4-carboxamide was stirred at room temperature for 16 hours. The reaction mixture was concentrated to dryness under reduced pressure and the residual syrup was admixed with 2.5 l. of water and triturated. The resultant crystals were washed and dried. By the above procedure there was obtained 355 g. of 5-amino-1-(2,3,5-tri-O-propionyl-β-D-ribofuranosyl)imidazole-4-carboxamide as crystals melting at 115°–116° C. A portion of this product was recrystallized from ethanol-diethyl ether, whereupon colorless needles melting at 117°–118° C. were obtained.

| Elemental analysis: | C(%) | H(%) | N(%) |
|---|---|---|---|
| Calculated for $C_{18}H_{26}N_4O_8$: | 50.70 | 6.15 | 13.14 |
| Found: | 50.60 | 6.10 | 13.21 |

(2) In a mixture of 1.12 l. of chloroform and 278 ml. of triethylamine was dissolved 170.4 g. of 5-amino-1-(2,3,5-tri-O-propionyl-β-D-ribofuranosyl)imidazole-4-carboxamide and, with stirring and ice-cooling, a solution of 39.6 ml. of phosphorus oxychloride in 360 ml. of chloroform was added dropwise over a period of 3 hours, the internal temperature being maintained not higher than 10° C. throughout the period. After the dropwise addition had been completed, the mixture was further stirred for 1.5 hours, at the end of which time it was poured in 400 ml. of ice water. The chloroform layer was taken and washed with 400 ml. of water twice, 400 ml. of 1 N-HCl twice and finally 200 ml. of a saturated aqueous solution of sodium chloride. The solution was dried over anhydrous sodium sulfate and concentrated to dryness. By the above procedure there was obtained 149 g. of 5-amino-4-cyano-1-(2,3,5-tri-O-propionyl-β-D-ribofuranosyl)imidazole as a syrupy residue.

Nuclear magnetic resonance spectrum (CDCl₃) δ (Hz): 1.17(9H, 3Me), 2.46(6H, 3—CH₂—), 4.50(3H, H4′, 5′), 5.20(2H, NH₂), 5.30–5.90(3H, H 1′, 2′, 3′), 7.40 (1H, H₂).

The above syrup was dissolved in a mixture of 280 ml. of methanol and 280 ml. of 25% aqueous ammonia and the solution was allowed to stand at room temperature for 5 hours. The reaction mixture was concentrated to dryness and the residue was washed with a small amount of methanol. By the above procedure there was obtained 63 g. of 5-amino-1-β-D-ribofuranosyl-4-cyanoimidazole as pale-yellow needles melting at 206°–208° C.

(3) In 1.5 l. of 20% methanolic ammonia, 100 g. of 5-amino-1-β-D-ribofuranosyl-4-cyanoimidazole and 110 g. of phenylcyanamide were heated at 180° C. for 5 hours in an autoclave. The reaction mixture was concentrated to dryness and the residue was washed with 500 ml. of ethanol and recrystallized from 10 l. of water. By the above procedure there was obtained 34 g. of N²-phenyl-2,6-diaminonebularine as brown needles. This product was recrystallized from 20% ethanol and, then, from boiling water to obtain colorless needles melting at 247°–248° C.

| Elemental analysis: | C(%) | H(%) | N(%) |
|---|---|---|---|
| Calculated for $C_{16}H_{18}N_6O_4$: | 53.62 | 5.06 | 23.45 |
| Found: | 53.45 | 4.99 | 23.24 |

EXAMPLE 2

In a manner similar to that of Example 1 (3), 4 g. of 5-amino-4-cyano-1-(2,3,5-tri-O-propionyl-β-D-ribofuranosyl)imidazole, 4 g. of phenylcyanamide and 50 ml. of 20% methanolic ammonia was reacted and treated to obtain 0.8 g. of N²-phenyl-2,6-diaminonebularine.

EXAMPLE 3

In a manner similar to that of Example 1 (3), 3.6 g. of 5-amino-4-cyano-1-(2,3,5-tri-O-acetyl-β-D-ribofuranosyl)imidazole, 5 g. of di-(p-chlorophenyl)carbodiimide and 40 ml. of 20% methanolic ammonia were reacted and treated to obtain 0.3 g. of N²-(p-chlorophenyl)-2,6-diaminonebularine as crystals melting at 165°–167° C.

| Elemental analysis: | C(%) | H(%) | N(%) |
|---|---|---|---|
| Calculated for $C_{16}H_{17}O_4N_6Cl \cdot H_2O$: | 46.77 | 4.66 | 20.46 |
| Found: | 47.08 | 4.27 | 20.62 |

EXAMPLE 4

In 40 ml. of pyridine were suspended 26 g. of 5-amino-1-β-D-ribofuranosylimidazole-4-carboxamide and 110 g. of benzoic anhydride and the suspension was stirred at 50° C. for 3 hours. The reaction mixture was concentrated and the residue was washed with 300 ml. of diethyl ether and dissolved in a mixture of 200 ml. of chloroform and 50 ml. of triethylamine. While the solution was stirred under ice-cooling, 80 ml. of a solution containing 8 ml. of phosphorus oxychloride in chloroform was added dropwise over a period of one hour.

After the dropwise addition had been completed, the reaction mixture was further stirred under ice-cooling for another 2 hours, at the end of which time it was poured in 100 ml. of ice water. The chloroform layer was taken, washed with 100 ml. of water twice, 100 ml. of 1 N-HCl twice and 50 ml. of saturated aqueous sodium chloride twice, and concentrated to dryness. To the residue was added diethyl ether and the mixture was allowed to stand. By the above procedure there was obtained 33 g. of crystals of 5-amino-4-cyano-1-(2,3,5-tri-O-benzoyl-β-D-ribofuranosyl)imidazole. A portion of the above product was recrystallized from ethanol to obtain crystals melting at 148°–150° C.

Infrared absorption spectrum (KBr): 2230 cm$^{-1}$ (—CN).

A mixture of 27 g. of the above crystals, 12 g. of phenylcyanamide and 100 ml. of 20% methanolic ammonia was heated at 180° C. for 3 hours in an autoclave. The reaction mixture was concentrated to dryness, the residue was dissolved in 300 ml. of 1 M-sodium ethoxide and the solution was allowed to stand at room temperature for 10 hours. The reaction mixture was then concentrated and 1 l. of ice water and 600 ml. of ethyl acetate were added. Under stirring, the mixture was brought to pH 2 with 1 N-HCl and the water layer was taken, neutralized and allowed to stand in the cold. By the above procedure there was obtained 5.3 g. of N²-phenyl-2,6-diaminonebularine as crystals.

EXAMPLE 5

In 100 ml. of 20% methanolic ammonia, 5 g. of 5-amino-1-β-D-ribofuranosyl-4-cyanoimidazole and 10 g. of dicyclohexylcarbodiimide were heated at 180° C. for 5 hours in an autoclave. The reaction mixture was concentrated to dryness and the residue was dissolved in 100 ml. of hot methanol and allowed to stand and cool. The crystalline precipitate was recrystallized from boiling water to obtain 1.5 g. of N²-cyclohexyl-2,6-diaminonebularine as colorless needles melting at 148°–150° C.

EXAMPLE 6

In 20 ml. of 20% methanolic ammonia, 1 g. of 5-amino-1-β-D-ribofuranosyl-4-cyanoimidazole and 2 ml. of diphenylcarbodiimide were heated at 180° C. for 5 hours in an autoclave. The reaction mixture was purified as in Example 1 to obtain 0.15 g. of N²-phenyl-2,6-diaminonebularine as colorless needles melting at 247°–248° C.

EXAMPLE 7

In a manner similar to that of Example 1 (3), 4 g. of 5-amino-1-β-D-ribofuranosyl-4-cyanoimidazole, 4.4 g. of triphenylmelamine (melting point: 210° C.) and 60 ml. of 20% methanolic ammonia were reacted and treated to obtain 1.4 g. of N²-phenyl-2,6-diaminonebularine as colorless needles.

EXAMPLE 8

In a manner similar to that of Example 1 (3), 2 g. of 5-amino-1-β-D-ribofuranosyl-4-cyanoimidazole, 2.3 g. of triphenylisomelamine (a molecular compound consisting of 2 moles of triphenylmelamine and 1 mole of phenylcyanamide: melting point; 185° C.) and 30 ml. of 20% methanolic ammonia were reacted and treated to obtain 0.65 g. of N²-phenyl-2,6-diaminonebularine as colorless needles.

EXAMPLE 9

In 150 ml. of 20% methanolic ammonia, 10 g. of 5-amino-1-β-D-ribofuranosyl-4-cyanoimidazole and 11 g. of phenylcyanamide were heated at 180° C. for 5 hours in an autoclave. The reaction mixture was concentrated to dryness and the residue was washed with 500 ml. of ethanol and recrystallized from 1 l. of water. By the above procedure there was obtained 3.4 g. of brown needles. This crystalline product was suspended in 50 ml. of 50% ethanol, the suspension was heated to 60° C. and 11 ml. of 1 N-HCl was added, whereby the crystals dissolved. This solution was concentrated to about 30 ml. and allowed to stand and cool. The resultant crystals were recrystallized from 50 ml. of 50% ethanol, whereupon 2.5 g. of N²-phenyl-2,6- diaminonebularine hydrochloride was obtained as colorless needles melting at 200°–205° C. (decomposition).

| Elemental analysis: | C(%) | H(%) | N(%) | Cl(%) |
|---|---|---|---|---|
| Calculated for | | | | |
| $C_{16}H_{18}N_6O_4 \cdot HCl \cdot H_2O$: | 46.55 | 5.13 | 20.34 | 8.60 |
| Found: | 46.42 | 5.09 | 20.42 | 9.05 |

EXAMPLE 10 TO 32

The N-substituted cyanimide described in Reference Example Table 1 were reacted in manners similar to that of Examples 1 (3), 2 or 4 to obtain the $N^2$-substituted-2,6-diaminonebularines (I) given in Table 2.

TABLE 2

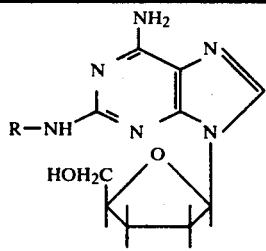

(I)

| Example | R | Molecular formula | Melting point (°C.) |
|---|---|---|---|
| 10 | 4-CH₃-C₆H₄- | $C_{17}H_{20}O_4N_6 \cdot \tfrac{1}{2}H_2O$ | 193–195 |
| 11 | 2-CH₃-C₆H₄- | $C_{17}H_{20}O_4N_6$ | 146–148 |
| 12 | 2-OCH₃-C₆H₄- | $C_{17}H_{20}O_5N_6 \cdot H_2O$ | 130–132 |
| 13 | 4-Br-C₆H₄- | $C_{16}H_{17}O_4N_6Br \cdot H_2O$ | 160–161 |
| 14 | 4-F-C₆H₄- | $C_{16}H_{17}O_4N_6F$ | 227 |
| 15 | 2-F-C₆H₄- | $C_{16}H_{17}O_4N_6F \cdot \tfrac{1}{2}H_2O$ | 134–136 |
| 16 | 4-C₂H₅-C₆H₄- | $C_{18}H_{22}O_4N_6$ | 167–169 |
| 17 | 3-CH₃-C₆H₄- | $C_{17}H_{20}O_4N_6$ | 231–232 |
| 18 | 3-CH₃O-C₆H₄- | $C_{17}H_{20}O_5N_6$ | 133–135 |
| 19 | 3-F-C₆H₄- | $C_{16}H_{17}O_4N_6F$ | 262–264 decomposition |
| 20 | 3-Cl-C₆H₄- | $C_{16}H_{17}O_4N_6Cl$ | 254–255 decomposition |
| 21 | 3-Br-C₆H₄- | $C_{16}H_{17}O_4N_6Br$ | 245–247 |
| 22 | 2,4-(CH₃)₂-C₆H₃- | $C_{18}H_{22}O_4N_6$ | 193–195 |
| 23 | 2-Cl-4-CH₃-C₆H₃- | $C_{17}H_{19}O_4N_6Cl$ | 250–251 |
| 24 | 2,4-(CH₃O)₂-C₆H₃- | $C_{18}H_{22}O_6N_6 \cdot \tfrac{1}{2}H_2O$ | 205–207 |
| 25 | 2-Cl-4-CH₃O-C₆H₃- | $C_{17}H_{29}O_5N_6Cl \cdot H_2O$ | 180–182 |
| 26 | 2-n-C₄H₉-C₆H₄- | $C_{20}H_{26}O_4N_6$ | 173 |
| 27 | 2,4-Cl₂-C₆H₃- | $C_{16}H_{16}O_4N_6Cl_2$ | 247–248 |
| 28 | 3,4-(CH₃)₂-C₆H₃- | $C_{18}H_{22}O_4N_6$ | 178–179 |
| 29 | 3,5-(CH₃)₂-C₆H₃- | $C_{18}H_{22}O_4N_6 \cdot \tfrac{1}{2}H_2O$ | 195–197 |
| 30 | 2,5-(CH₃)₂-C₆H₃- | $C_{18}H_{22}O_4N_6 \cdot \tfrac{1}{2}H_2O$ | 150 |
| 31 | 2-Cl-6-OCH₃-C₆H₃- | $C_{17}H_{19}O_5N_6Cl \cdot H_2O$ | 245–247 |
| 32 | 2,6-Cl₂-C₆H₃- | $C_{16}H_{16}O_4N_6Cl_2$ | 238–240 |

EXAMPLE 33

In 9.6 l. of methanol were dissolved 800 g. of 5-amino-1-β-D-ribofuranosyl-4-cyanoimidazole and 1 kg. of phenylcyanamide, and following addition of 2.4 l. of liquid ammonia, the solution was heated at 150° C. (as the internal temperature) under shaking for 5 hours in an autoclave of 20 l. capacity. The reaction mixture was concentrated to dryness and the residue was washed with 4 l. of ethanol and recrystallized from 80 l. of water to obtain 360 g. of $N^2$-phenyl-2,6-diaminoebularine as brown needles.

What is claimed is:

1. A method for producing a compound of the formula

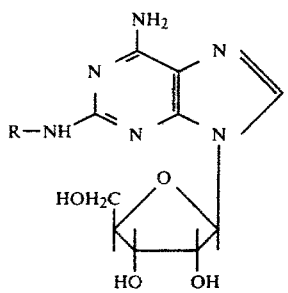

wherein R is phenyl, substituted phenyl, cyclohexyl or substituted cyclohexyl the substituent being halogen, lower alkyl or lower alkoxy, or an acid addition salt thereof, which comprises reacting 5-amino-1-β-D-ribofuranosyl-4-cyanoimidazole with a compound of the formula:

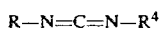

wherein R is as defined above and R⁴ is hydrogen or the same group as R.

2. A method according to claim 1, wherein the reaction is conducted in the presence of ammonia.

3. A method according to claim 1 or 2, wherein R is phenyl or phenyl substituted by halogen, lower alkyl or lower alkoxy.

4. A method according to claim 3, wherein R is phenyl.

5. A method according to claim 1 or 2, wherein the compound of the formula R—N=C=N—R⁴ is phenylcyanamide.

6. A method for producing a compound of the formula

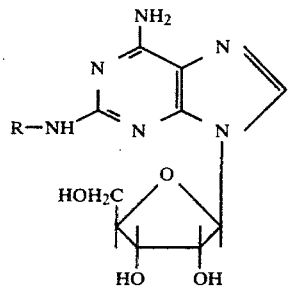

wherein R is phenyl, substituted phenyl, cyclohexyl or substituted cyclohexyl, the substituent being halogen, lower alkyl or lower alkoxy, or an acid addition salt thereof, which comprises reacting 5-amino-1-β-D-ribofuranosylimidazole-4-carboxamide with a reactive derivative of a carboxylic acid, dehydrating the resulting 5-amino-1-[2,3,5-tri-O-(carboxylic acid-derived acyl)-β-D-ribofuranosyl]imidazole-4-carboxamide to yield 5-amino-4-cyano-1-[2,3,5-tri-O-(carboxylic acid-derived acyl)-β-D-ribofuranosyl]imidazole, treating 5-amino-4-cyano-1-[2,3,5-tri-O-(carboxylic acid-derived acyl)-β-D-ribofuranosyl]imidazole with a base to yield 5-amino-1-β-D-ribofuranosyl-4-cyanoimidazole and reacting 5-amino-1-β-D-ribofuranosyl-4-cyanoimidazole with a compound of the formula

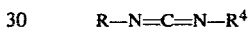

wherein R is as defined above and R⁴ is hydrogen or the same group as R.

7. A method according to claim 6, wherein R is phenyl.

8. A method according to claim 6, wherein the carboxylic acid contains up to 7 carbon atoms.

9. A method according to claim 6, wherein the carboxylic acid-derived acyl is propionyl.

10. A method for producing N²-phenyl-2,6-diaminonebularine, which comprises reacting 5-amino-1-β-D-ribofuranosylimidazole-4-carboxamide with a reactive derivative of propionic acid to yield 5-amino-1-(2,3,5,-tri-O-propionyl-β-D-ribofuranosyl)imidazole-4-carboxamide, dehydrating 5-amino-1-(2,3,5-tri-O-propionyl-β-D-ribofuranosyl)imidazole-4-carboxamide to yield 5-amino-4-cyano-1-(2,3,5-tri-O-propionyl-β-D-ribofuranosyl)imidazole, treating 5-amino-4-cyano-1-(2,3,5-tri-O-propionyl-β-D-ribofuranosyl)imidazole with aqueous ammonia or alkali metal alkoxide to yield 5-amino-1-β-D-ribofuranosyl-4-cyanoimidazole and reacting 5-amino-1-β-D-ribofuranosyl-4-cyanoimidazole with phenylcyanamide in the presence of ammonia to yield N²-phenyl-2,6-diaminonebularine.

* * * * *